(12) United States Patent
Hennink et al.

(10) Patent No.: US 11,007,148 B2
(45) Date of Patent: May 18, 2021

(54) AMPHIPHILIC BLOCK COPOLYMERS FOR DELIVERY OF ACTIVE AGENTS

(71) Applicant: Rheinisch-Westfälische Technische Hochschule (RWTH) Aachen, Aachen (DE)

(72) Inventors: Wilhelmus Everhardus Hennink, Utrecht (NL); Yang Shi, Utrecht (NL); Cornelus Franciscus van Nostrum, Utrecht (NL)

(73) Assignee: Rheinisch-Westfälische Technische Hochschule (RWTH) Aachen, Aachen (DE)

( * ) Notice: Subject to any disclaimer, the term of this patent is extended or adjusted under 35 U.S.C. 154(b) by 0 days.

(21) Appl. No.: 15/503,204

(22) PCT Filed: Aug. 11, 2015

(86) PCT No.: PCT/NL2015/050574
§ 371 (c)(1),
(2) Date: Feb. 10, 2017

(87) PCT Pub. No.: WO2016/024861
PCT Pub. Date: Feb. 18, 2016

(65) Prior Publication Data
US 2017/0231908 A1    Aug. 17, 2017

(30) Foreign Application Priority Data
Aug. 11, 2014  (NL) ..................................... 2013317

(51) Int. Cl.
| | | |
|---|---|---|
| *C08F 293/00* | (2006.01) | |
| *A61K 49/00* | (2006.01) | |
| *A61K 49/12* | (2006.01) | |
| *A61K 9/107* | (2006.01) | |
| *A61K 47/34* | (2017.01) | |
| *A61K 31/337* | (2006.01) | |
| *A61K 31/47* | (2006.01) | |
| *A61K 31/506* | (2006.01) | |
| *A61K 31/573* | (2006.01) | |
| *A61K 31/704* | (2006.01) | |
| *A61K 38/13* | (2006.01) | |

(52) U.S. Cl.
CPC .......... *A61K 9/1075* (2013.01); *A61K 31/337* (2013.01); *A61K 31/47* (2013.01); *A61K 31/506* (2013.01); *A61K 31/573* (2013.01); *A61K 31/704* (2013.01); *A61K 38/13* (2013.01); *A61K 47/34* (2013.01); *C08F 293/00* (2013.01); *C08F 293/005* (2013.01)

(58) Field of Classification Search
None
See application file for complete search history.

(56) References Cited

U.S. PATENT DOCUMENTS

| | | | |
|---|---|---|---|
| 2003/0143184 A1* | 7/2003 | Seo ...................... | A61K 31/337 424/78.17 |
| 2004/0247670 A1* | 12/2004 | Hennink ............... | A61K 9/1075 424/468 |
| 2005/0158271 A1* | 7/2005 | Lee ........................ | A61K 9/145 424/78.3 |
| 2010/0247654 A1 | 9/2010 | Hsiue et al. | |
| 2011/0152167 A1 | 6/2011 | Hedrick et al. | |
| 2011/0237700 A1* | 9/2011 | Miyabayashi ....... | C09D 11/101 522/64 |
| 2011/0281934 A1* | 11/2011 | Johnson ............... | A61K 9/1075 514/44 A |

FOREIGN PATENT DOCUMENTS

| | | |
|---|---|---|
| ES | 2 391 187 | 11/2012 |
| JP | 2004-534879 A | 11/2004 |
| JP | 2005-514500 A | 5/2005 |
| JP | 2010-275349 A | 12/2010 |
| WO | 2009/094053 A1 | 7/2009 |

OTHER PUBLICATIONS

Yang et al., Biomacromol., 2013, 14(6), pp. 1826-1837.*
Shi et al., Biomacromol., 2013, 14(6), pp. 1826-1837. (Year: 2013).*
De Graff et al., J. Control. Release, 2012, vol. 162, pp. 582-590. (Year: 2012).*
International Search Report dated Nov. 19, 2015 for Appln. No. PCT/NL2015/050574.
Yang et al., "[Pi]-[Pi] Stacking increases the stability and loading capacity of thermosensitive polymeric micelles for chemotherapeutic drugs", Biomacromolecules, vol. 14, No. 6, Jun. 10, 2013, pp. 1826-1837.
Chiang et al. "Polymer-liposome complexes with a functional hydrogen-bond cross-liner for preventing protein adsorption and improving tumor accumulation", vol. 25, No. 21, Nov. 12, 2013, pp. 4364-4372.

(Continued)

*Primary Examiner* — Brian Gulledge
(74) *Attorney, Agent, or Firm* — Pillsbury Winthrop Shaw Pittman, LLP

(57) ABSTRACT

The present invention provides an amphiphilic block copolymer for drug delivery and a controlled release system comprising the same copolymer. The copolymer comprises at least one hydrophilic block and at least one hydrophobic block, wherein the hydrophobic block is selected from the group consisting of acrylates, methacrylates, acrylamides, methacrylamides, vinylethers and their aromatic derivatives, wherein at least one hydrophobic block contains an aryl group, which is bound to the hydrophobic block with a degradable linker. The controlled release system of the invention shows high stability and high drug retention when administered in vivo enabling accumulation and drug release at the site of action.

16 Claims, 8 Drawing Sheets

(56) References Cited

OTHER PUBLICATIONS

Notice of Reasons for Refusal dated Jun. 11, 2019 issued in corresponding Japanese Patent Application No. 2017-508049 with English translation.
Communication pursuant to Article 94(3) EPC dated Nov. 3, 2020 issued in corresponding European Patent Application No. 15767355.9 (6 pgs.).

* cited by examiner dexamethasone:

DAPT:

DOX.HCl:

imatinib free base:

bedaquiline:

cyclosporine A:

paclitaxel:

mPEG-p(HPMAm-Bz):

mPEG-b-p(BHMPO):

AMPHIPHILIC BLOCK COPOLYMERS FOR DELIVERY OF ACTIVE AGENTS

CROSS-REFERENCE TO RELATED APPLICATIONS

This is the U.S. National Stage of PCT/NL2015/050574, filed Aug. 11, 2015, which in turn claims priority to Netherlands Application No. 2013317, filed Aug. 11, 2014, the entire contents of both applications being incorporated herein by reference in their entireties.

The invention relates to a novel class of polymers for encapsulation and in vivo drug delivery. Another aspect of the invention is a controlled release system for active ingredients (active agents) comprising such polymers.

Amphiphilic polymers are known to be used in encapsulation systems in the form micelles in an aqueous environment with a hydrophobic core, in which the hydrophobic drug can be captured.

Desired characteristics of the micelles carrying a drug are a high stability of the loaded micelle and good retention of the drug (prolonged circulation in blood), when administered in a body after, e.g., intravenous administration.

In the prior art, methods have been developed for covalent encapsulation of drugs in polymeric micelles. In covalent encapsulation, active ingredients such as drug molecules are chemically bonded to the polymer chains. This, however, has a disadvantage that organic synthesis needs to be performed to couple the drug molecules to high molecular weight polymer chains (with consequent challenges), and the necessity to develop a new polymer for each drug molecule which limits the applicability of a new polymer platform technology. Covalent encapsulation can also be performed by cross-linking, however this may have some disadvantages. For example, the release of the drug has to occur by degradation of the linker that connects the drug and carrier which is sometimes difficult to control resulting in insufficient concentration of the drug at the aimed site of action.

Even if some systems show good stability in vitro, it may appear that the stability in vivo is not sufficient. Without wishing to be bound by any theory, it is hypothesized that some serum proteins may be able to bind amphiphilic polymer molecules which can disrupt the dynamic equilibrium of micelles and unimers. Therefore, it is difficult to predict whether a particular system would show sufficient stability in in vivo tests.

Another important property is a sufficient retention of the drug in the micelle after administration, which corresponds to a prolonged circulation of the encapsulated drug in blood. Many drugs generally have a short half-life in the human or animal body. Therefore, multiple daily injections or continuous infusions would be required to have a desired therapeutic effect. This is why systems for controlled or sustained release are very desirable for such purposes.

It is therefore desired to provide a polymer suitable for use in controlled delivery systems to encapsulate particularly hydrophobic active ingredients, which systems have a high stability in vivo and show good retention of the drug when administered into a body, and which avoid the disadvantages of the covalent entrapment of the drug.

BRIEF DESCRIPTION OF THE INVENTION

In order to address at least some of the above needs, the present invention provides, in one aspect, a block copolymer comprising at least one hydrophilic block and at least one hydrophobic block, wherein the hydrophobic block is selected from the group consisting of acrylates, methacrylates, acrylamides, methacrylamides, vinylethers and their aromatic derivatives, wherein at least one hydrophobic block contains an aromatic side group, which is bound to the hydrophobic block with or through a degradable linker, wherein the aromatic side group is an aryl.

In another aspect, the present invention provides a controlled release system comprising the block copolymer according to the invention and a physically entrapped active ingredient.

DETAILED DESCRIPTION OF THE INVENTION

Figure 1:
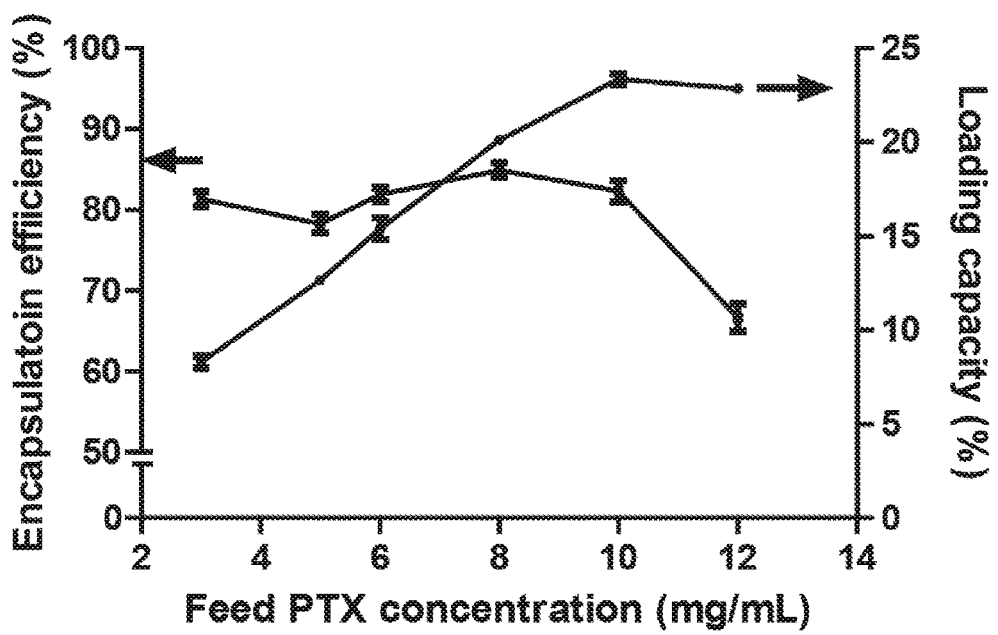
FIG. 1 shows the encapsulation efficiency (%) and loading capacity (%) of the loaded micelles according to the invention plotted against the feed PTX concentration (mg/mL). PTX is paclitaxel, which is used as a model drug.

The present invention is based on the judicious insight that the stability of polymer micelles and retention of a hydrophobic drug physically entrapped in the micelles can be increased when using a particular polymer with aromatic side groups. It is surprising to obtain highly stable micelles with long circulation in blood for drugs that only physically entrapped in the micelles. Without wishing to be bound by any theory, it is believed by the inventors that the aromatic side groups on the polymeric chains provide for increased physical binding with the drug molecules, especially when the latter contain themselves aromatic groups so that aromatic interactions between the polymer chains and the drug molecules are possible. Also aromatic interactions between the polymer chains aid to their stability in the circulation.

In the present description and the appending claims, the term "copolymer" means a polymer wherein at least two types of monomers are present. "Amphiphilic" means possessing both hydrophobic and hydrophilic properties.

The term "active ingredient" includes therapeutic and diagnostic agents. Therapeutic agents are compounds capable of exerting a preventive, therapeutic or pharmacological action in a human or animal body. Under preventive or therapeutic actions are usually understood beneficial effects of interactions with or effect on a cell tissue in a human or animal body. Appropriate diagnostics-related active ingredients include those useful for angiography, MRI, CT scan imaging, nuclear magnetic resonance imaging, radiography, X-ray contrast imaging, ultrasound, etc. Particular diagnostic active ingredients are, for example, photosensitizers, imaging agents (such as MRI contrast agents), radioisotope compounds, fluorescent compounds, dyes.

"Hydrophobic" means having a partition coefficient log P in octane-water higher than 1. For the definition of log P reference is made to Chemical Reviews 1971, volume 71, number 6.

"Physical" entrapment of the active ingredient molecules is used here as synonym of "non-covalent" bonding. "Non-covalent interaction" means any interaction which is not covalent, i.e. any weak bonding between atoms or bonds which bonding does not involve the sharing of electron pairs. Examples of non-covalent interaction are hydrophobic, aromatic (n-n), hydrogen bonding, electrostatic, stereo complex, and metal-ion interactions. Entrapment is also used as a synonym for binding, loading or encapsulation of the active ingredient.

"Linker" means a chemical group having functionality to connect different parts (or building blocks) of a molecule, typically two parts. Degradable means in this context biodegradable. "Hydrolysable" means degradable by means of hydrolysis. "Physiological conditions" are the conditions present in an organism to be treated with the controlled release system of the invention; for humans these conditions encompass a pH of about 7.4 and a temperature of about 37° C.

The copolymer according to the present invention is a block copolymer comprising at least one hydrophilic block and at least one hydrophobic block. The copolymer is therefore an amphiphilic block copolymer. In aqueous solutions, these polymers form micelles with a hydrophobic core, which can be loaded, particularly with hydrophobic drugs. The copolymer of the invention is suitable for use in controlled release systems, target delivery systems and others used inside a human or animal body. In some embodiments, this may mean that the copolymer of the invention is a bioresorbable polymer or it converts to a bioresorbable polymer after hydrolysis, which means that the polymer material is safely absorbed by the body and it disappears from the body over time.

The polymers of the present invention can have all possible polymer architectures, such as (multi-)block copolymers (such as AB, ABA, ABAB, etc.) or graft copolymers, random copolymers or terpolymers, or a polymeric networks; all of which may be grafted.

The hydrophobic block contains monomers that are preferably selected from the group of acrylates, methacrylates, acrylamides, methacrylamides, vinylethers and derivatives thereof. More preferably, the hydrophobic block contains methacrylamide or its derivatives, more preferably hydroxyalkyl methacrylamide. For derivatives particularly aromatic derivatives are preferred, which means that the derivative contains an aromatic group, more preferably an aryl or a substituted aryl. Examples of preferred monomers include 2-hydroxyethyl methacrylate (HEMA), 2-hydroxyethyl acrylate (HEA), glyceryl methacrylate or glycidyl methacrylate (GMA), glyceryl acrylate or glycidyl acrylate (GA), hydroxypropyl methacrylamide (HPMAAm).

At least one hydrophobic block of the copolymer of the invention contains an aromatic side group, coupled through a degradable linker. Aromatic means that the side group contains at least one aromatic ring. Aromatic includes heteroaryls and aryl groups. Heteroaryls contain heteroatoms such as N or S in at least one ring and are optionally substituted. Aryl means throughout this description and the claims a monocyclic or polycyclic aromatic hydrocarbon group derived from the corresponding arene by removal of a hydrogen atom from a ring carbon atom, which is optionally substituted. Examples of suitable aromatic groups are phenyl, naphthyl, indoyl and their derivatives. Examples of particularly suitable aryl groups are phenyl and naphthyl. Also arylalkyl groups are suitable, such as arylmethyl (particularly, phenyl) and other arylalkyl groups with C1-C4 carbon atoms in the alkyl moiety. In some embodiments, the aromatic side group is preferably an aryl or an arylalkyl group. Preferably, the aromatic group is benzyl, phenyl or naphthyl or derivatives thereof, more preferably phenyl or naphthyl.

Preferably, the aromatic group is present in more than 25 mol. % of the side groups of the monomers that form the hydrophobic blocks, more preferably at least 50 mol. %. Yet more preferably, at least 75 mol. % of monomers of the hydrophobic blocks contain the aromatic group and most preferably, 100 mol. % of monomers of the hydrophobic blocks.

In a particular embodiment, the hydrophobic block of the copolymer of the invention does not contain lactate groups. Lactate groups mean a monolactate, a dilactate or an oligolactate group. A lactate can be used to provide the copolymer with thermosensitive properties. Thermosensitive copolymers with N-(2-hydroxypropyl)methacrylamide monolactate as a part of the hydrophobic block were reported in Y. Shi et al., Biomacromolecules 2013, 14, 1826-1837. However, when the present inventors tested these paclitaxel loaded micelles in vivo they observed a half-life of the drug of less than 2 minutes pointing to a rapid destabilization of these thermosensitive micelles and/or a rapid release of the drug from the micelles. In contrast, the half-life of the micelles according to the invention loaded with the same drug paclitaxel is about 8 hours. Reference is made to Example 3 and FIG. 3 in the present application.

In the present invention use is made of a degradable linker for the coupling of the aromatic side group to the polymer backbone of the hydrophobic block. This ensures a constant release of this group together with the physically entrapped active ingredient. The linker is preferably degradable under physiological conditions, and more preferably it is hydrolysable under physiological conditions. But the linkers might also be hydrolyzed by the actions of enzymes. Generally, known linkers can be used, selected from esters, orthoesters, amides, carbonates, carbamates, anhydrides, ketals, acetals, hydrazone and derivatives thereof. In some embodiments, an ester linker is used, preferably of formula —C(O)—O—. In that case, the phenyl group together with the ester linker forms a benzoyl group, and the naphthyl group together with the ester linker—a naphthoyl group. In yet other embodiments, hydrazone linkers are used. Hydrazone linkers contain a group —C=N—N—.

In a special embodiment of the present invention a pH-sensitive linker is used. Preferably, such linker hydrolyzes at a pH less than 7, more preferably at a pH of 6.5 or less.

An advantage of a pH-sensitive linker is that it can selectively release the entrapped drug at areas with an increased acidity, such as some tumors or inflammation sites. Also degradation of the micelles and release of entrapped drug might occur in endosomes or lysosomes having a lower pH, after cellular binding and internalization of the drug-loaded micelles.

Particularly preferred are hydrazone linkers with the following general formula:

wherein $R_1$, $R_2$ can be independently of each other H or alkyl groups, and wherein $R_3$ is an alkyl group or a ketone group —C(O)—. Preferably, the alkyl group is a $C_1$-$C_3$ alkyl. More preferably, $R_1$ or $R_2$ is a methyl group. In a preferred embodiment, $R_3$ is a ketone group —C(O)—.

As hydrophilic block of the copolymer of the invention any suitable polymer can be used. Preferably, the hydrophilic block comprises a polyalkylene glycol, more preferably a polyethylene glycol (PEG).

The weight ratio of the hydrophobic to hydrophilic block is preferably in the range from 10:90 to 90:10, more preferably from 40:60 to 60:40.

The copolymer can be prepared by starting from a mixture of the monomers and carrying out the polymerization reaction. Preferably, the copolymer is obtained by radical polymerization. It is also possible to first produce the copolymer and subsequently functionalize it by coupling suitable groups. Methods of synthesis of copolymers are known to a skilled person. An example of a suitable method to synthesize monomers is described in Y. Shi et al., Biomacromolecules 2013, 14, 1826-1837. An example of a synthesis of macroinitiator that can be used in the polymerization reaction is described in D. Neradovic et al. Macromolecules, 2001, 34 (22), pp 7589-7591.

A preferred embodiment of the present invention is the use of the copolymer of the invention in or as a controlled release system which system further comprises at least one physically entrapped active ingredient.

Therefore, in another aspect, the invention provides a controlled release system comprising the block copolymer according to any one of the preceding claims and at least one physically entrapped active ingredient.

Preferably, the polymer is in the form of a polymeric micelle having a hydrophobic core and the active ingredient is physically entrapped in the hydrophobic core of the micelle. The amphiphilic block copolymers of the present invention are particularly suitable to form a controlled release system in the form of polymeric micelles. Polymeric micelles are, in turn, particularly suitable for encapsulation and controlled and targeted release of hydrophobic active ingredients because they can be entrapped in the hydrophobic core of the micelle.

The micelles of the present invention are also particularly suitable for targeted drug delivery; that is, they can selectively accumulate at the site of action such as inflamed tissue due to the EPR effect (Enhanced Permeability and Retention effect; reference is made to Maeda, H.; Nakamura, H.; Fang, J. Advanced Drug Delivery Reviews 2013, 65, (1), 71-79.).

As demonstrated in the examples, the micelles according to the invention loaded with paclitaxel show slow release from the micelles (50% of loading in about 10 days) demonstrating a good retention of the drug in the micelles. The micelles also show long blood circulation time (half-time of around 8 hours). The PTX-loaded micelles showed full inhibition of the tumor growth in mice, whereas at an equal dose the commercially used Taxol® formulation of PTX was much less effective.

The polymeric micelles of the invention are rather monodisperse. In some embodiments, the micelles have a size 20-100 nm. This refers to Z-average hydrodynamic diameter, as measured by dynamic light scattering. The polydispersity index PDI is preferably less than 0.3, more preferably less than 0.15, as measured by dynamic light scattering.

The active ingredient is preferably a therapeutic or diagnostic agent. As mentioned above, more active ingredients can be loaded (entrapped) in the same system. In a particular embodiment of the present invention, the controlled release system comprises two active ingredients. These can be for example two therapeutic agents, which is particularly useful in combination therapy where several drugs are administered simultaneously. Another embodiment is a system comprising a therapeutic agent and a diagnostic agent such as an imaging agent (e.g. MRI contrast agent).

In some embodiments, it is preferred that the active ingredient molecule contains at least one aromatic group. In such cases, it was observed that the loaded micelles are particularly stable and have high retention of the drug in vivo. Without wishing to be bound by any theory, it is believed that this for a part could be explained by enhanced aromatic interaction between the aromatic side groups of the polymer chains and of the drug molecules.

In a preferred embodiment, the type of active ingredient to be entrapped, includes but is not limited to, drug molecules, for example of the (gluco)corticosteroid type or of the chemostatic type, peptides/proteins, imaging agents, genetic material or a combination of these. Particularly, the drugs preferably include anticancer or cytostatic drugs, corticosteroids, antibiotics, anti viral drugs. Active ingredients of different chemical origin can be entrapped in the polymeric micelles of the present invention. Particularly, the present invention is beneficial for entrapping hydrophobic active ingredients, with or without aromatic groups, which usually have significant problems with delivery due to the poor aqueous solubility. An example of a hydrophobic active ingredient without aromatic groups is dexamethasone. Examples of hydrophobic active ingredients with aromatic groups are bedaquiline and paclitaxel. The hydrophobic active ingredients to be encapsulated have preferably a log P of at least 1, more preferably at least 1.5. The aqueous solubility of the active ingredient is preferably less than 5 mg/ml.

Also non-hydrophobic active ingredients can successfully be encapsulated, e.g. amphiphilic compounds carrying a charge such as salts. An example of this is doxorubicin hydrochloride. Other examples of active ingredients that were found to be successfully entrapped in the micelles of the present invention include DAPT (notch inhibitor) and cyclosporin A (immunosuppressant).

In a particularly preferred embodiment of this use, the controlled release system releases paclitaxel as active ingredient.

The controlled release system of the present invention is suitable for treatment of diseases characterized by inflammation and increased vascular permeability. Such diseases include but are not limited to the diseases selected from the group consisting of cancer, infection, ophthalmological diseases, viral infection, bacterial infection, fungal infection, mucoplasma infection, parasite infection, inflammation, dermatological diseases, cardiovascular diseases, diseases of the central nerve system, auto-immune diseases, proliferative diseases, arthritis, psychotic diseases, psoriasis, diabetes, metabolic disorders, lung diseases, respiratory diseases, pulmonary diseases, COPD, diseases of the muscoskeletal system, emphysema, edema, hormonal diseases. The controlled release system of the present invention is also suitable for delivery of anesthetics, to be used in vaccination, being either therapeutic or preventive.

For the purpose of clarity and a concise description features are described herein as part of the same or separate embodiments, however, it will be appreciated that the scope of the invention may include embodiments having combinations of all or some of the features described.

The invention will now be illustrated in the following, non-limiting examples. Parts and percentages mentioned in the examples and through the description, are by weight, unless otherwise indicated. In the working examples, the mean particle size ($Z_{ave}$) and polydispersity index (PDI) of the micelles was determined with dynamic light scattering (DLS) using a Malvern ALV/CGS-3 Goniometer. $^1$H-NMR spectra were recorded with a Gemini 300 MHz spectrometer (Varian Associates Inc., NMR Instruments, Palo Alto, Calif., USA).

EXAMPLES

Example 1 Copolymer Synthesis

Copolymer poly(ethylene glycol)-b-(N-(2-benzoyloxypropyl) methacrylamide)) (mPEG-b-p(HPMAm-Bz)) was synthesized using mPEG2-ABCPA as macroinitiator and HPMAm-Bz as monomer. The monomer has been synthesized following the procedure described in Y. Shi et al., Biomacromolecules 2013, 14, 1826-1837. The phenyl group is attached through an ester linker to the HPMA monomer. The macroinitiator synthesis is described in D. Neradovic et al., Macromolecules, 2001, 34 (22), pp 7589-7591).

The monomer was dissolved at a concentration of 0.3 g/mL in acetonitrile (dried on A4 molecular sieves) and the molar ratio of monomer-to-macroinitiator was 200/1. The solution was degassed by flushing with nitrogen for 30 minutes. The reaction was conducted at 70° C. for 24 hours under a nitrogen atmosphere. The polymer was purified by precipitation in diethyl ether and this dissolution/precipitation procedure was repeated twice. The polymer was dried under vacuum at room temperature for 24 hours and collected as a white powder.

The number average molecular weight (Mn) of the synthesized polymers was 20,000 Da by gel permeation chromatography (GPC) analysis (PDI being Mw/Mn was 1.7) and 22,000 Da by $^1$H NMR analysis. The content of PEG in the copolymer is ~23 wt. % (5,000 Da of PEG and 17,000 Da of the hydrophobic block based on the NMR analysis). The critical micelle concentration (CMC) of the polymer was 1.3 µg/mL as measured using pyrene as the probe according to a method reported in Langmuir, 2004, 20 (21), pp 9388-9395.

Similar procedure was followed to prepare a naphthoyl derivative, mPEG-b-p(HPMAm-Nt), using mPEG2-ABCPA as macroinitiator and HPMAm-Nt as monomer. The molar ratio of monomer-to-macroinitiator was 250/1.

Example 2 Preparation of Micelles

Empty mPEG-b-p(HPMAm-Bz) micelles were prepared as follows. mPEG-b-p(HPMAm-Bz) was dissolved in THF at a concentration of 27 mg/mL and subsequently, 1 mL of the polymer solution was added dropwise to 1 mL of reverse osmosis (RO) water while stirring. The mixture was incubated at room temperature for 48 hours to allow evaporation of THF. The resulting micellar dispersion was filtered through 0.45 µm nylon membrane (Acrodisc®).

Figure 10:
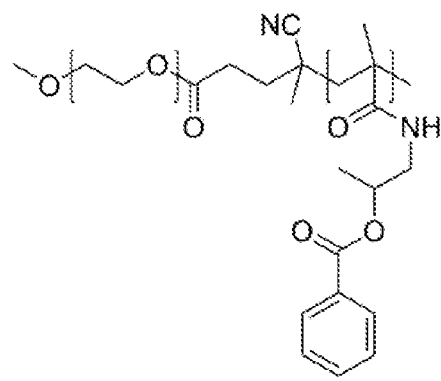
FIG. 10 shows the chemical formulae of mPEG-p(HPMAm-Bz) and mPEG-b-p(BHMPO).
Figure 10:
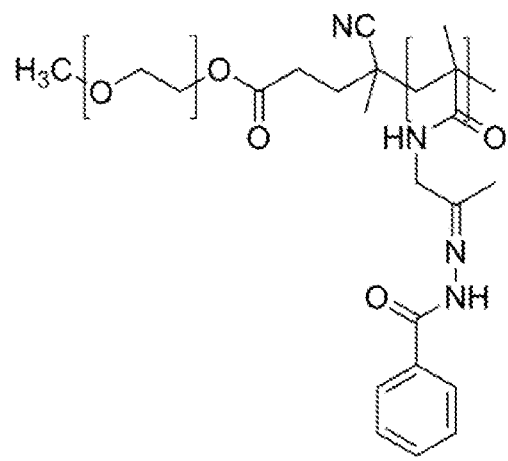

Paclitaxel (PTX)-loaded micelles were prepared as follows. PTX and mPEG-b-p(HPMAm-Bz) (structure shown in FIG. 10) were dissolved in THF with PTX concentration ranging from 3 to 12 mg/mL and 27 mg/mL for the polymer. 1 mL of the polymer solution was added dropwise to 1 mL of reverse osmosis (RO) water while stirring. The mixture was incubated at room temperature for 48 hours to allow evaporation of THF. The resulting micellar dispersion was filtered through 0.45 µm nylon membrane (Acrodisc®).

The measuring of the loading capacity, encapsulation efficiency, size and size distribution (DPI) of the PTX-loaded micelles were performed according to the procedure described in Y. Shi et al., Biomacromolecules 2013, 14, 1826-1837. The results are shown in FIGS. 1 and 2.

FIG. 1 shows the encapsulation efficiency (%) and loading capacity (%) of the loaded micelles against the feed PTX concentration (mg/mL).

Figure 2:
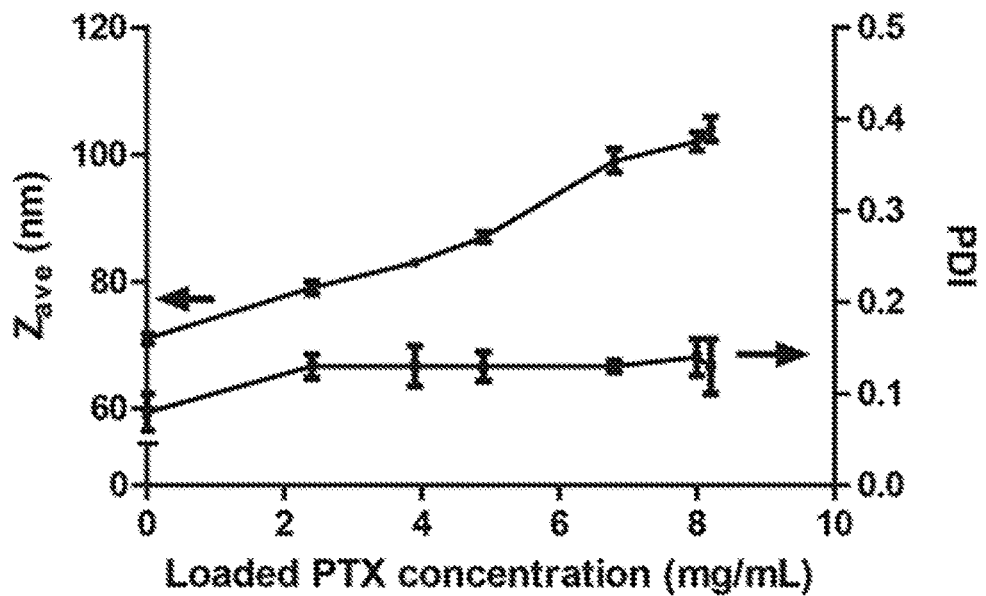
FIG. 2 shows Z-average hydrodynamic diameter ($Z_{ave}$, nm) and polydispersity index (PDI) of the loaded micelles according to the invention as measured by dynamic light scattering plotted against the loaded PTX concentration (mg/mL).

FIG. 2 shows Z-average hydrodynamic diameter ($Z_{ave}$, nm) and polydispersity index (PDI) of the loaded micelles against the loaded PTX concentration (mg/mL) measured by dynamic light scattering. As can be seen from the figure, the polymeric micelles of the invention are rather monodisperse and preferably have a size of ~70-100 nm with a polydispersity index PDI less than 0.15.

The results show that up to a feed concentration of PTX of 10 mg/ml, the drug encapsulation efficiency was very good (>80%), leading to a formulation with a high drug loading (~25% (w/w) at a feed concentration of 10 mg/ml.

Example 3 In Vivo Studies

Human A431 tumor Xenografts were established by subcutaneous inoculation of the mice in the right flank with 1×106 A431 cells suspended in 100 µL PBS pH 7.4. Tumors were measured using a digital caliper. The tumor volume V in mm$^3$ was calculated using the formula V=($\pi$/6)LS$^2$ where L is the largest and S is the smallest superficial diameter. When the tumors reached a volume of 80-100 mm$^3$, mice were included in the study. The mice were injected with 100 µL of the PTX-loaded micelles (3.2 mg/mL PTX and 27 mg/mL polymer) via the tail vein.

Plasma concentrations of PTX after i.v. injections of different PTX formulations in A431 human tumor-bearing female Crl:NU-Fox$^{nu}$1nu mice (22.5±2.5 g) mice (n=7-8) were measured in time.

The four formulations included PTX loaded micelles of the invention mPEG-b-p(HPMAm-Bz) obtained according to Example 2 and three comparative formulations, being PTX loaded in thermosensitive micelles mPEG-b-p(HPMAm-Bz$_{30}$-co-HPMAm-Lac$_{70}$) and mPEG-b-p(HPMAm-Nt$_{25}$-co-HPMAm-Lac$_{75}$), and commercially available Taxol®. The results are shown in FIG. 3.

Figure 3:
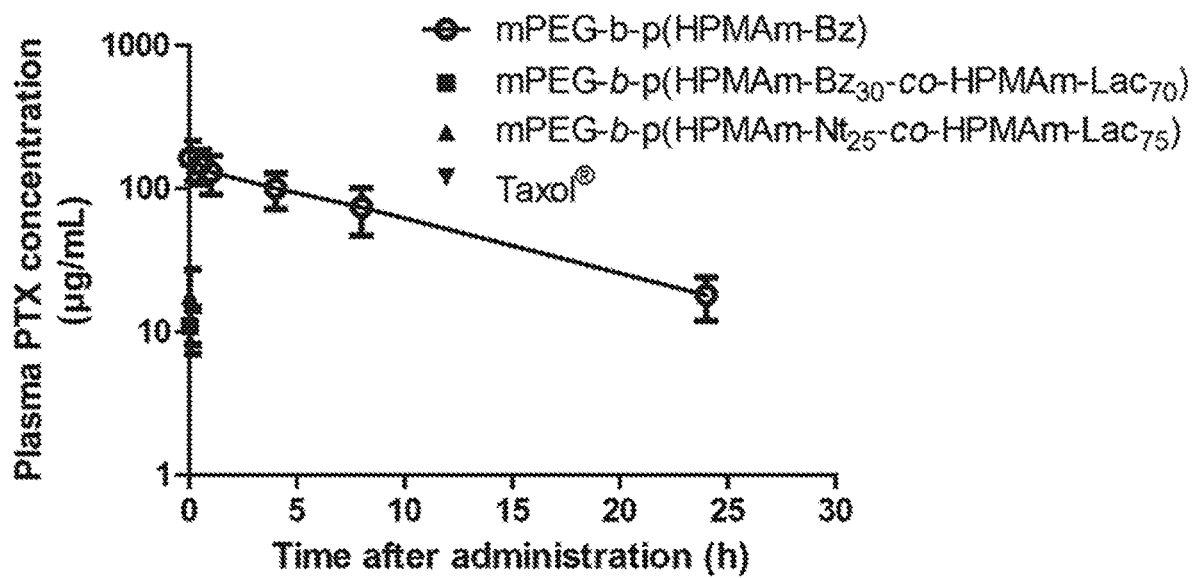
FIG. 3 shows plasma concentrations of PTX after i.v. injections of four different PTX formulations in A431 human tumor-bearing female Crl:NU-Fox$^{m}$1nu mice, measured in time.

As seen in FIG. 3, the PTX concentrations in blood samples from mice received Taxol® or thermosensitive mPEG-b-p(HPMAm-Bz/Nt-co-HPMAm-Lac) micelles were below detection limit (<0.6 μg/mL plasma) 24 hours post injection. It has been estimated that the half-life of drug administered as formulation of thermosensitive micelles was less than 2 minutes.

It can be concluded that the amphiphilic block copolymer according to the invention forms stable micelles with excellent retention of the loaded PTX.

Figure 4:
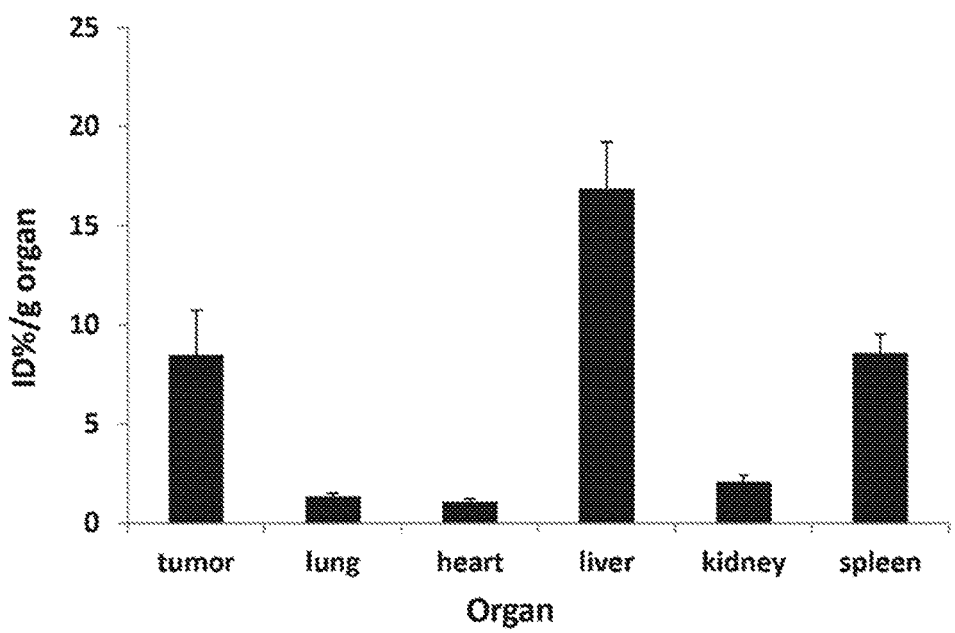
FIG. 4 shows the injected dose (ID) in %/g organ in different organs of the mice 24 hours after i.v. injection of PTX-loaded mPEG-b-p(HPMAm-Bz) micelles.

FIG. 4 shows the injected dose (ID) in %/g organ in different organs of the mice 24 hours after i.v. injection of PTX-loaded mPEG-b-p(HPMAm-Bz) micelles. The PTX concentrations in organs (tumor, lungs, heart, liver, kidneys and spleen) of mice that received Taxol® and PTX-loaded thermosensitive mPEG-b-p(HPMAm-Bz/Nt-co-HPMAm-Lac) micelles was below detection limit (<0.4 ID %/g organ) (n=8).

Example 4 In Vivo Kinetic Studies

In this example the kinetic properties of loaded micelles with PTX are studied in vivo using the fluorophore labels Cy7 and Cy5.5. Cy7 was covalently linked to the polymer chain and reports about the fate of the injected micelles; Cy5.5 was physically loaded in the core of the micelles and used as a modal drug.

mPEG-b-p(HPMAm-Bz-co-AEMAm) was synthesized according to Example 1 with 2 mol. % of AEMAm (N-(2-aminoethyl)methacrylamide hydrochloride, relative to HPMAm-Bz copolymerized in the hydrophobic block of the polymer. The primary amine side groups of mPEG-b-p (HPMAm-Bz-co-AEMAm) were subsequently reacted with Cy7 NHS ester. For that, Cy7 NHS ester was dissolved in DMSO (dried on 4 angstrom molecular sieves) at a concentration of 10 mg/mL. The polymer (31 mg) was transferred into dried flask and, 0.18 mL solution of the Cy7 NHS ester (10 mg/mL) and 1 μL of TEA (dried on 4 angstrom molecular sieves) were added and the reaction was conducted at 50° C. for 48 hours. Uncoupled Cy7 was removed by dialysis against THF/water (1/1, v/v) with refreshing the dialysate after 24 hours for in total 5 times. The final product was collected after freeze drying and obtained as a dark green powder after lyophilization.

mPEG-b-p(HPMAm-Bz) micelles chemically labeled with Cy7 and physically loaded with Cy5.5 were prepared similarly to the PTX-loaded mPEG-b-p(HPMAm-Bz) micelles described in Example 2. Briefly, 1 mL THF solution of 26.6 mg of non-labeled mPEG-b-p(HPMAm-Bz), 0.4 mg of Cy7 labeled mPEG-b-p(HPMAm-Bz) and 0.02 mg of Cy5.5 (as a physically loaded modal drug) was added dropwise to 1 mL of water while stirring. The micellar dispersion was incubated at room temperature for 48 hours to allow evaporation of THF. Next, the resulting micellar dispersion was filtered through 0.45 μm nylon membrane (Acrodisc®).

CD-1 nude female mice (n=5) were fed with chlorophyll-free food pellets and water ad libitum, and caged in ventilated cages and clinically controlled rooms and atmosphere. The animal studies were performed in compliance with guidelines set by national regulations and were approved by the local animal experiments ethical committee. CD-1 nude mice were inoculated with A431 tumor cells (4×10$^6$ cells/100 μL PBS pH 7.4) subcutaneously into the right flank 15 days before the start of the experiment, which lead to the development of A431 tumor xenograft with an approximate size of 6-7 mm in width.

Figure 5:
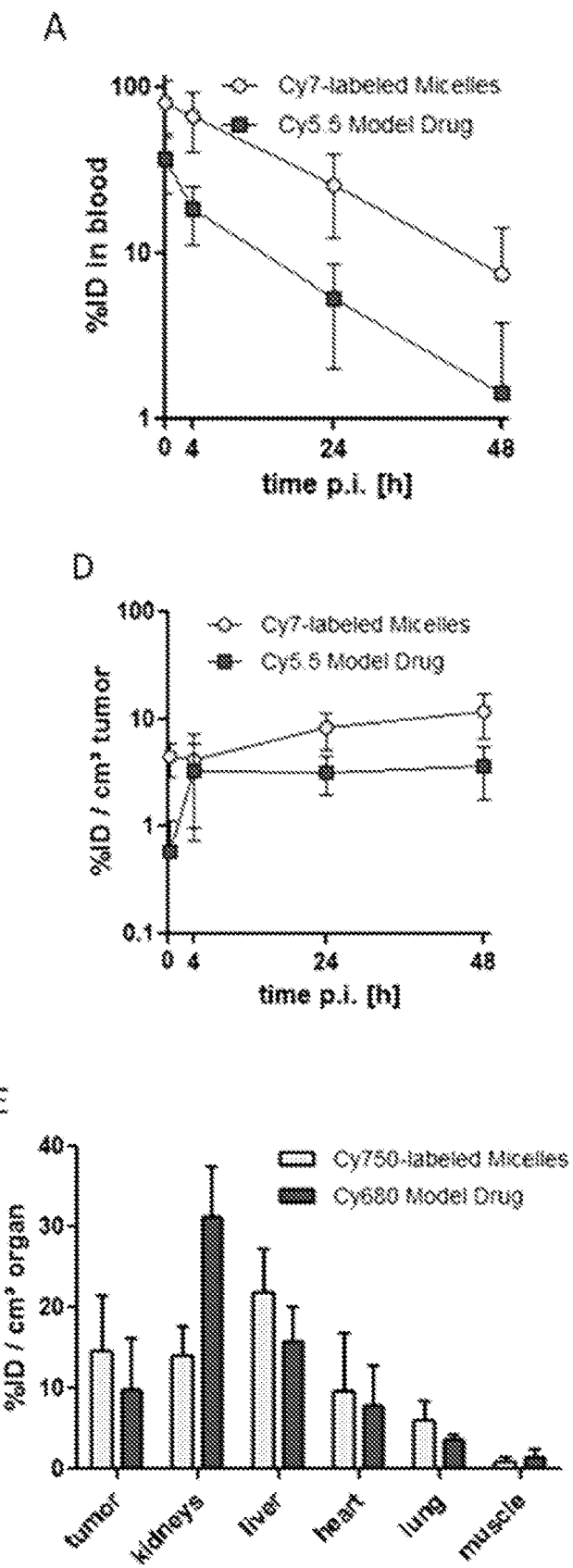
FIG. 5A shows the injected dose (% ID in blood) plotted against the time p.i. (post injection) in hours.
FIG. 5D shows the injected dose to the volume of the tumor (% ID/cm$^3$ of the tumor) plotted against the post injection time (h).
FIG. 5E shows the injected dose to the volume of the organ (% ID/cm$^3$ organ) for different organs of the mice. Model drug is PTX.

FIG. 5 shows circulation kinetics, tumor accumulation and in vivo biodistribution of the Cy7-labeled mPEG-b-p (HPMAm-Bz) micelles loaded with Cy5.5 (n=5) as a modal drug. In FIG. 5A the injected dose (% ID in blood) is shown against the time p.i. (post injection) in hours. In FIG. 5D, the injected dose to the volume of the tumor (% ID/cm$^3$ of the tumor) is shown against the post injection time (h). FIG. 5E shows the injected dose to the volume of the organ (% ID/cm$^3$ organ) for different organs of the mice. Model drug is Cy5.5.

Since the Cy7 label is covalently linked to the polymer, it reports about the fate of the injected micelles. It is clear that in line with the plasma kinetic data of PTX (FIG. 3) the micelles have a half-life around 8 hours. The Cy5.5 label shows a shorter half-life, most likely because this compound is more hydrophilic and consequently shows less retention in the micelles than PTX.

Figure 6:
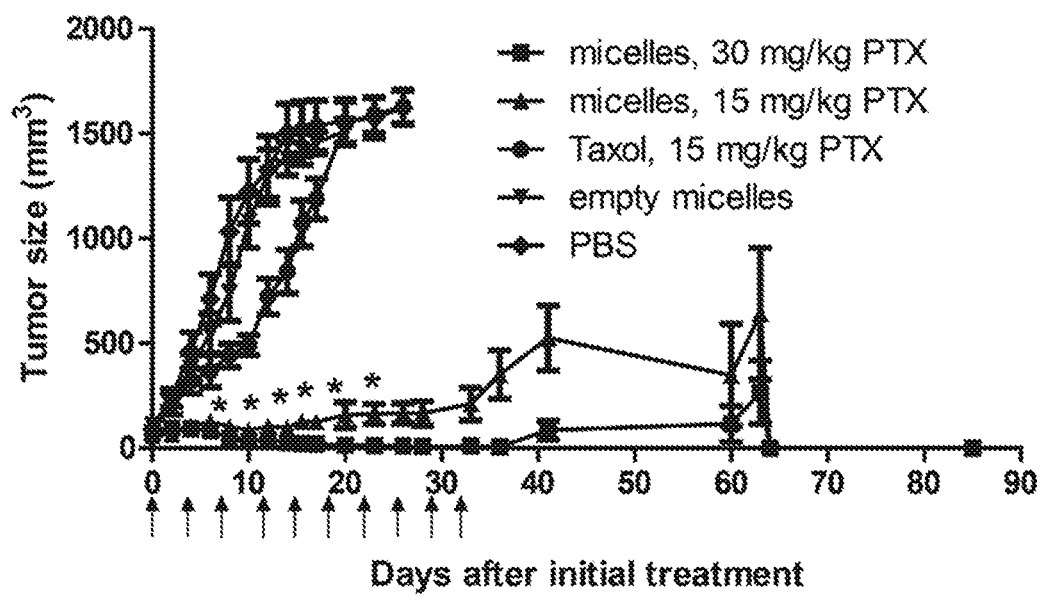
FIG. 6 shows the development of the tumor size in mm$^3$ in the days after initial treatment for the micelles of the invention and for comparative systems being Taxol®, empty micelles and phosphate-buffered saline PBS solution.

FIG. 6 shows the development of the tumor size in mm$^3$ in the days after initial treatment. The lower two curves represent the data of the micelles of the invention loaded with PTX. The three other curves provide the data obtained with commercially available Taxol®, empty micelles and PBS as comparative data.

Human A431 tumor growth in female Crl:NU-Fox$^{n u}$1nu mice (22.5±2.5 g) was treated with i.v. injections of PBS, empty mPEG-b-p(HPMAm-Bz) micelles, Taxol® (15 mg/kg PTX) and PTX-loaded mPEG-b-p(HPMAm-Bz) micelles (15 and 30 mg/kg PTX) (upper) (n=12). After that, Kaplan-Meier survival curves of A431 tumor-bearing mice treated with PTX formulations or negative control (n=12) were plotted (FIG. 7).

Figure 7:
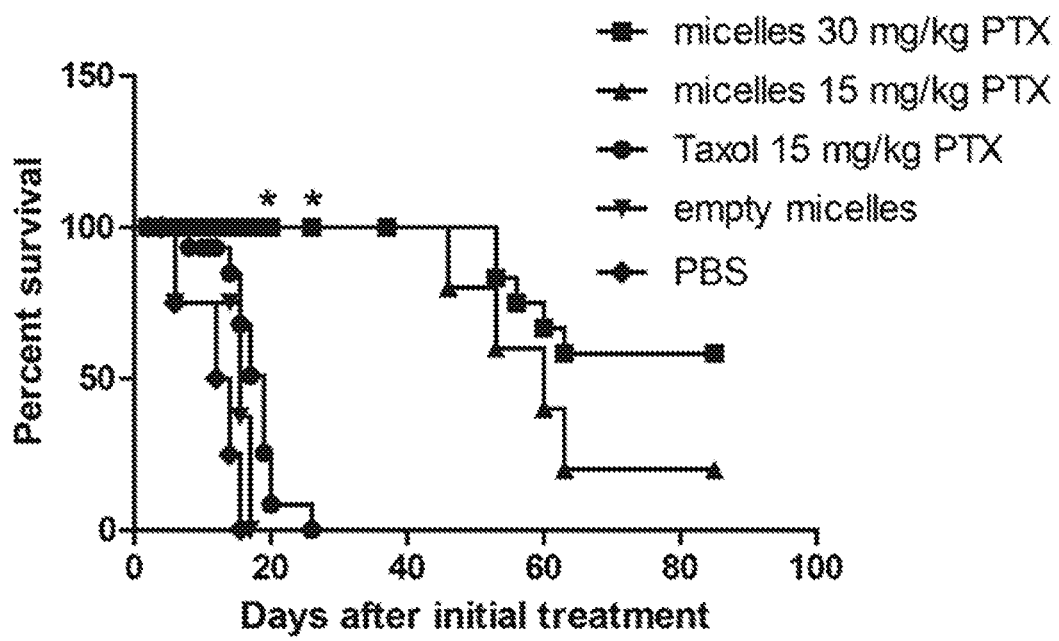
FIG. 7 shows % survival plotted against the days after initial treatment with the loaded micelles with PTX according to the invention and comparative systems being Taxol®, empty micelles and phosphate-buffered saline PBS solution.

FIG. 7 shows % survival plotted against the days after initial treatment with the loaded micelles with PTX according to the invention and comparative systems.

The results show that the therapeutic efficiency of the polymeric micellar formulations are impressive. Complete tumor regression was observed at 36 day for the animals that received the high dose of micellar formulations (30 mg PTX/kg). Also the low dose micellar formulation (15 mg PTX/kg) show a substantial and better antitumor effect than an equal dose of the commercial Taxol® formulation.

Example 5 In Vivo Studies, Slowly Growing Tumor

Similar to Example 4, the therapeutic efficacy of the PTX-loaded mPEG-b-p(HPMAm-Bz) micelles was studied in mice bearing MDA-MB-468 breast carcinoma xenografts. In this study mice received similar treatments as in the A431 study (Example 4) but i.v. injections were administered once a week rather than every other day. Treatment was initiated 4 weeks after inoculation with the tumor cells, when tumors had reached a volume of ~100 mm$^3$.

Figure 8:
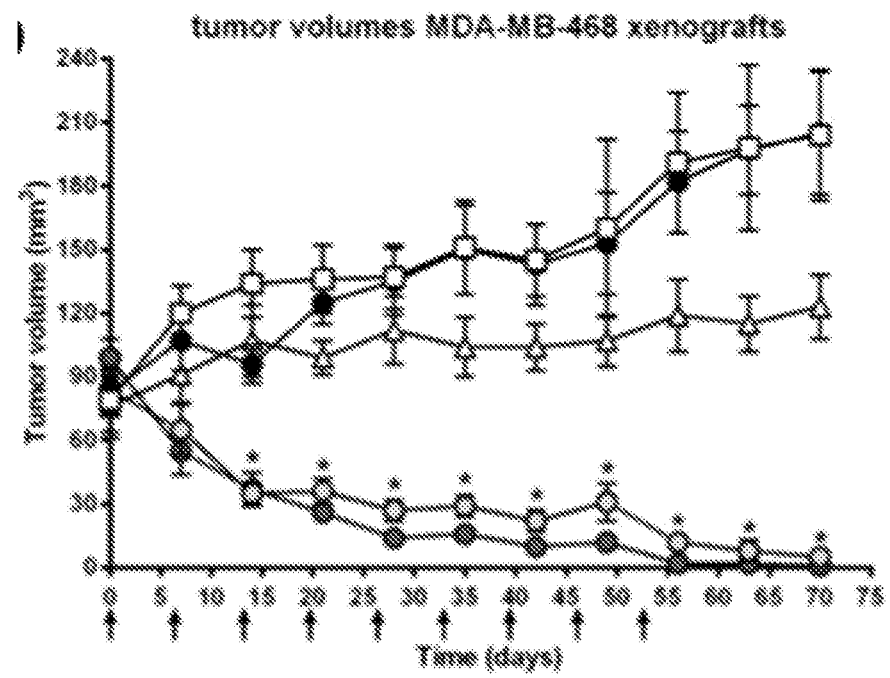
FIG. 8 shows the development of the tumor size MDA-MB-468 xenografts in mm$^3$ in the days after initial treatment for the micelles of the invention with PTX (15 mg/kg and 30 mg/kg) and for comparative systems being Taxol®, empty micelles and phosphate-buffered saline PBS solution. The arrows show the i.v. injections.

FIG. 8 shows the development of the tumor size in mm$^3$ in the days after initial treatment. The lower two curves represent the data of the micelles of the invention loaded with PTX. The three other curves provide the data obtained with commercially available Taxol®, empty micelles and PBS as comparative data. Arrows represent i.v. injections.

FIG. 8 shows that Taxol® (15 mg/kg PTX) only slightly inhibited tumor growth, while the tumors of mice that received the PTX-loaded micelles (15 and 30 mg/kg PTX) decreased in volume and completely regressed after 60 days. These results confirm the potent therapeutic efficacy of the PTX-loaded polymeric micelles observed in the study with A431 as a tumor model.

Repeated injections of PTX-loaded polymeric micelles were generally well tolerated and mice did not suffer from significant weight loss throughout the course of the therapeutic efficacy studies. Furthermore, no organ toxicities were observed for the empty or PTX-loaded polymeric micelles, as representatively assessed for liver, spleen and kidney by histopathological analysis. These observations suggest a favorable toxicity profile for the micellar formulation.

As shown in these examples, the controlled release system of the invention is an attractive carrier system for the development of PTX-nanomedicines. The polymeric micelles are produced in a straightforward and cost-effective manner, without the need for chemical crosslinking or covalent drug conjugation, and are characterized by excellent loading capacity, enhanced stability and strong PTX retention. The $IC_{50}$ values of micellar PTX were comparable to those of the free drug (i.e. Taxol®), for both A431 and MDA-MB-468 cells, indicating that the potency of PTX was not compromised by encapsulation. The micellar characteristics ensure prolonged circulation kinetics, substantial tumor accumulation and efficient tumor regression in two well-known and routinely used xenograft models, i.e. A431 and MDA-MB-468, without inducing significant toxicity, demonstrating the therapeutic (and translational) potential of this formulation.

Example 6 Encapsulation of Different Active Agents

Figure 9:
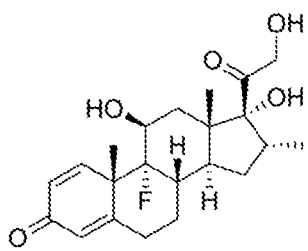
FIG. 9 shows chemical formulae of encapsulated active agents.
Figure 9:
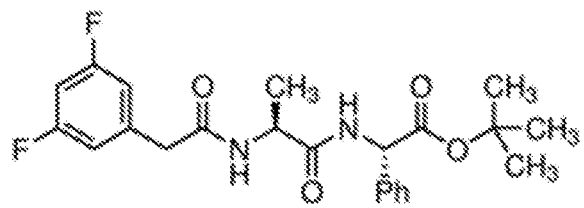
Figure 9:
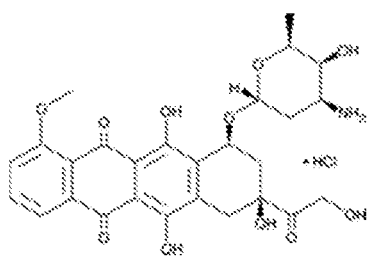
Figure 9:
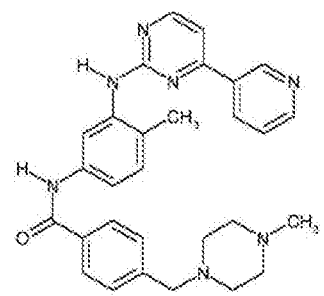
Figure 9:
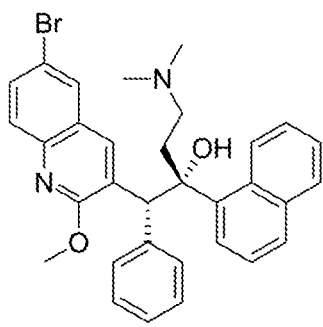
Figure 9:
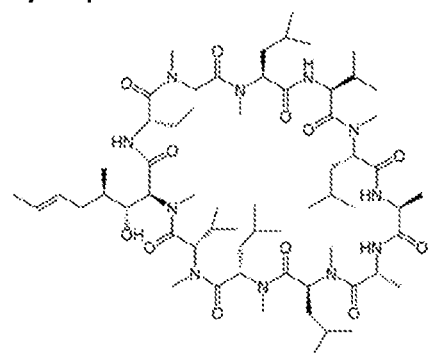
Figure 9:
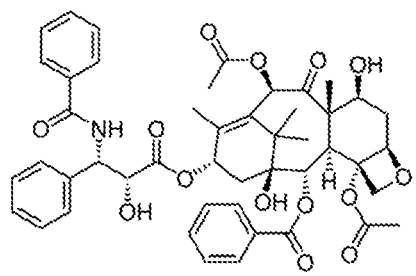

The encapsulation procedure was followed to encapsulate different drugs from the list: dexamethasone, doxorubicin hydrochloride (DOX.HCl), bedaquiline, DAPT and cyclosporin A. The polymers used are mPEG-b-p(HPMAm-Bz) with batch numbers J01 ($M_n$ 48.000, [monomer]/[initiator]=600/1) and J02 ($M_n$ 59.000, [monomer]/[initiator]=1000/1), and J03 being mPEG-b-p(HPMAm-Nt)$_{250}$ (Mn 32.000, [monomer]/[initiator]=250/1). The molecular weight $M_n$ is determined by NMR. The chemical formulae for the active agents are shown in FIG. 9.

Preparation of the drug loaded micellar formulations: 1 mL of tetrahydrofuran in which 5 mg of polymer and 1 mg of drug/drug candidate were dissolved was added dropwise to 1 mL reverse osmosis (RO) water with stirring and the mixture was kept stirring for 1 more minute. The mixtures were placed in fume hood overnight to evaporate tetrahydrofuran. The drug-loaded micellar dispersions (except the dox formulations) were filtered via 0.45 µm membrane and the filtrates were analyzed by DLS (size of the formed micelles) and dissolved in acetonitrile (1 volume of micellar dispersion was added to 19 volumes of acetonitrile) for encapsulation efficiency (EE) and loading capacity (LC) measurements by UV-Visible spectroscopy (all drugs except for paclitaxel that was analyzed by HPCL). For DOX.HCl—loaded micelles, the formulations were centrifuged using vivaspin tubes at 10000 g for 5 minutes and the non-loaded drug in the filtrate was quantified by UV-Visible spectroscopy to calculate the EE and LC. The results are presented in Table 1.

TABLE 1

| Drug | Log P | Polymer | $Z_{ave}$ (nm) | PDI | EE (%) | LC (%) |
|---|---|---|---|---|---|---|
| Dexamethasone | 1.83 | J02 (Bz) | 89 | 0.15 | 89 | 15.1 |
| Dexamethasone | 1.83 | J01 (Bz) | 92 | 0.14 | 77 | 13.3 |
| DOX•HCl | 2.82 | J02 (Bz) | 90 | 0.10 | 92 | 15.5 |
| Bedaquiline | 7.59 | J02 (Bz) | 97 | 0.20 | 46 | 8.4 |
| DAPT | 3.54 | J02 (Bz) | 80 | 0.09 | 61 | 10.9 |
| Imatinib free base | 4.61 | J02 (Bz) | 88 | 0.16 | 70 | 12.3 |
| Cyclosporin A | 4.37 | J02 (Bz) | 85 | 0.14 | 64 | 11.3 |
| Paclitaxel | 4.7 | J03 (Nt) | 96 | 0.15 | 73 | 12.7 |

The table shows that drugs and drug candidates with log P>1 can successfully be loaded in the polymeric micelles with high EE and LC. These include drugs having aromatic groups (PTX, bedaquiline, DOX.HCl, DAPT and imatinib free base), hydrophobic drugs without aromatic groups (dexamethasone and cyclosporine A), drug (candidates) with aromatic groups and also with charged groups (DOX.HCl, imatinib free base and bedaquiline). In addition to polymers with benzoyl groups of different molecular weight, this table shows a good EE and LC for a polymer modified with naphthyl groups (PEG-p(HPMAm-Nt)$_{250}$) for paclitaxel.

Example 7 pH-Sensitive Micelles

Synthesis of 1-[2-(2-benzoylhydrazono)propylamino]-2-methyl-2-propen-1-one (BHMPO)

In a flask dried overnight at 180° C., 1-(acetonylamino)-2-methyl-2-propen-1-one (AMPO, 677 mg, 4.8 mmol) and 4-methoxyphenol (polymerization inhibitor, 6 mg; 0.05 mmol) were dissolved in 146 mL of methanol (dried on A4 molecular sieves) under nitrogen atmosphere at room temperature. AMPO was synthesized according to the method described in ACS Biomater. Sci. Eng., 2015, 1 (6), pp 393-404. BH (626 mg, 4.6 mmol) was added to this solution. After 5 minutes of stirring, 7.5 mL of glacial acetic acid was added to the solution and the reaction was kept stirring under nitrogen atmosphere for 24 hours at room temperature. The solvent was removed under reduced pressure and the crude product was purified by silica column chromatography (40 g) with an eluent of hexane/ethyl acetate (1/9, v/v). The fractions that contained the compound with $R_f$ of 0.4 (hexane/ethyl acetate (1/1, v/v)) were collected and the solvents were removed under reduced pressure. The final product was collected as a yellow powder with a yield of 834 mg (71%), and the melting point was 164° C., which was measured by differential scanning calorimetry (Discovery, TA Instruments). The structure was confirmed by $^1$H NMR analysis using a Gemini 300 MHz spectrometer (Varian Associates Inc. NMR Instruments, Palo Alto, Calif.), using DMSO-d6 as the solvent; the DMSO peak at 2.52 ppm was used as the reference line. Chemical shifts (DMSO-d6): 11.3 (s, C=N—NH—CO), 8.7 (t, CO—NH—CH2), 7.9 (d, 2H, aromatic CH), 7.5 (m, 3H, aromatic CH), 5.7 and 5.4 (s, CH2=C), 4.0 (d, NH—CH2-C), 2.0 (s, CH3-C=C), 1.9 (s, CH2-C(CH3)=N).

Synthesis of mPEG-b-p(BHMPO)

A block copolymer of mPEG-b-p(BHMPO) was synthesized via a macroinitiator route using mPEG2-ABCPA as macroinitiator and BHMPO as monomer. The monomer was dissolved at a concentration of 0.3 g/mL in DMSO (dried on A4 molecular sieves) and the molar ratio of monomer-tomacroinitiator was 200/1. The solution was degassed by flushing with nitrogen for 30 minutes. The reaction was conducted at 70° C. for 24 hours under a nitrogen atmosphere. The polymer was purified by precipitation in diethyl ether and this dissolution/precipitation procedure was repeated twice. The polymer was dried under vacuum at room temperature for 24 hours and collected as a pale-yellow powder.

Formulations Preparation

Paclitaxel (PTX)-loaded mPEG-b-p(BHMPO) (23 kDa, by NMR; structure shown in FIG. 10) micelles were prepared by as follows: 1 mL solution of PTX (4 mg) and the polymer (27 mg) in THF/MeOH (=tetra hydrofuran/methanol) (1/1, v/v) was added dropwise to 1 ml RO water while stirring, 10 μL of phosphate buffer pH 7.4 (1 M) was added to the mixture to adjust the pH to 7.4. The micellar dispersion was incubated at room temperature for 24 hours to evaporate the organic solvents. Next, the micellar dispersion was filtered through a 0.45 μm membrane. The size of the formed micelles was determined using Dynamic Light Scattering analysis and the PTX loading was determined by HPLC. The PTX concentration was measured to be 3.3 mg/ml, encapsulation efficiency (EE) 83%, particle size 83 nm, PDI 0.08.

pH-Dependent Stability of the Empty mPEG-b-p (BHMPO) Micelles

The empty mPEG-b-p(BHMPO) micelles were prepared using the above method, without adding PTX. The pH of the micellar dispersion was adjusted to 5.0 or 6.5 by diluting the micelles 5 times in 150 mM ammonium acetate buffer at pH 5.0 or $NaH_2PO_4$ buffer at pH 6.5, respectively. The pH dependent stability of the empty mPEG-b-p(BHMPO) micelles at different pH values and 37° C. was studied by monitoring the size and the light scattering intensity of the micelles by DLS. The results are shown in FIG. 11.

Figure 11:
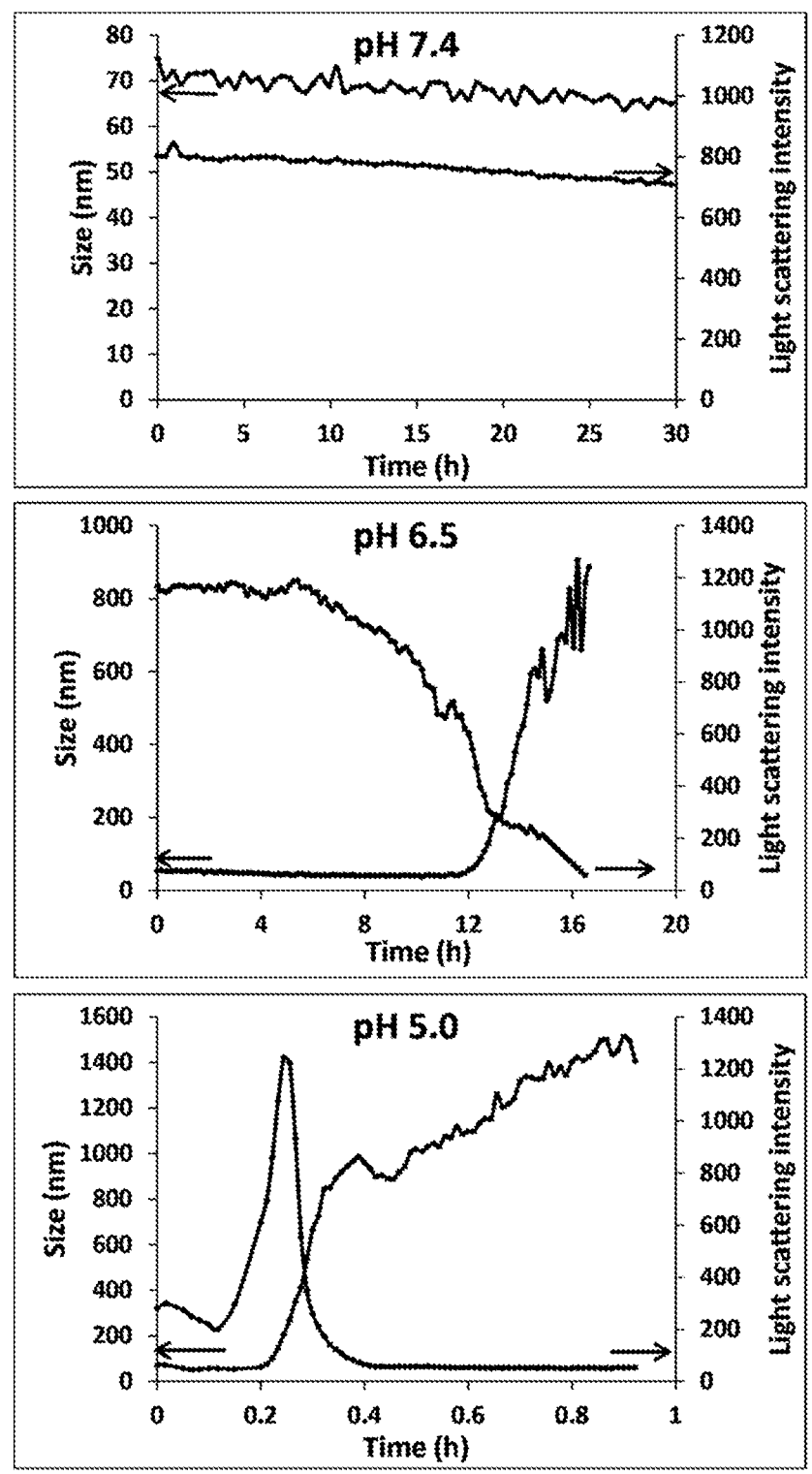
FIG. 11 shows the size and light scattering intensity measured by DLS as a function of time, for empty micelles of mPEG-b-p(BHMPO) at pH 7.4, 6.5 and 5.0.

As can be seen in FIG. 11, the hydrazone bonds between the benzoyl groups and the polymer backbone are sensitive to acidic pH values (6.5 and 5.0), while stable at neutral pH (7.4). Therefore the micelles are expected to be stable in the blood circulation and degrade specifically in tumor tissues and cells, by which PTX loaded in the micelles can be released to kill the tumor cells.

The invention claimed is:

1. A block copolymer comprising at least one hydrophilic block and at least one hydrophobic block, wherein the hydrophobic block is selected from the group consisting of acrylates, methacrylates, acrylamides and methacrylamides, wherein the acrylates, methacrylates, acrylamides or methacrylamides contain an aryl side group which is coupled to the polymer backbone of the hydrophobic block with a degradable linker, wherein the aryl side group is unsubstituted phenyl, benzyl or naphthyl, wherein the hydrophobic block of the copolymer does not contain lactate groups, and wherein more than 75 mol. % of monomers of the hydrophobic block contain the aromatic side group, wherein at least one of the at least one hydrophilic block comprises a polyethylene glycol, and wherein at least one of the at least one hydrophobic block comprises a N-(2-benzoyloxypropyl)(meth)acrylamide.

2. The copolymer according to claim 1, wherein the hydrophobic block comprises at least one additional optional monomer selected from the group consisting of 2-hydroxyethyl methacrylate, 2-hydroxyethyl acrylate, glyceryl methacrylate, glycidyl methacrylate, glyceryl acrylate, glycidyl acrylate, and hydroxypropyl methacrylamide.

3. The copolymer according to claim 1, wherein the at least one hydrophilic block comprises polyethylene glycol.

4. The copolymer according to claim 1, wherein the degradable linker is selected from esters, orthoesters, amides, carbonates, carbamates, anhydrides, ketals, acetals, hydrazone and their derivatives.

5. The copolymer according to claim 4, wherein the degradable linker is an ester or a hydrazone linker.

6. A controlled release system comprising the block copolymer according to claim 1 and at least one physically entrapped active ingredient.

7. The controlled release system according to claim 6, wherein the polymer is in the form of a polymeric micelle having a hydrophobic core and the active ingredient is physically entrapped in the hydrophobic core of the micelle.

8. The controlled release system according to claim 6, wherein the active ingredient is hydrophobic or amphiphilic.

9. The controlled release system according to claim 6, wherein the active ingredient is a therapeutic agent or a diagnostic agent.

10. The controlled release system according to claim 6, wherein the active ingredient is selected from the group consisting of: dexamethasone, DAPT, doxorubicin, imatinib, bedaquiline, cyclosporine A, and paclitaxel.

11. The controlled release system according to claim 9, comprising two active ingredients, being either two therapeutic agents or a therapeutic agent and a diagnostic agent.

12. The controlled release system according to claim 10, wherein the active ingredient is paclitaxel.

13. The controlled release system according to claim 6, wherein the hydrophobic block comprises at least one additional optional monomer selected from the group consisting of 2-hydroxyethyl methacrylate, 2-hydroxyethyl acrylate, glyceryl methacrylate, glycidyl methacrylate, glyceryl acrylate, glycidyl acrylate, and hydroxypropyl methacrylamide.

14. The controlled release system according to claim 7, wherein the active ingredient is hydrophobic or amphiphilic.

15. The controlled release system according to claim 7, wherein the active ingredient is a therapeutic agent or a diagnostic agent.

16. The controlled release system according to claim 7, wherein the active ingredient is selected from the group consisting of: dexamethasone, DAPT, doxorubicin, imatinib, bedaquiline, cyclosporine A, and paclitaxel.

* * * * *